(12) United States Patent
Axén et al.

(10) Patent No.: US 7,244,301 B2
(45) Date of Patent: Jul. 17, 2007

(54) HEAT GENERATING BIOCOMPATIBLE CERAMIC MATERIALS

(75) Inventors: Niklas Axén, Järlåsa (SE); Leif Hermansson, Uppsala (SE); Dan Markusson, Växjö (SE); Tobias Persson, Uppsala (SE)

(73) Assignee: Doxa AB, Uppsala (SE)

( * ) Notice: Subject to any disclaimer, the term of this patent is extended or adjusted under 35 U.S.C. 154(b) by 0 days.

(21) Appl. No.: 10/673,250

(22) Filed: Sep. 30, 2003

(65) Prior Publication Data

US 2004/0117030 A1 Jun. 17, 2004

(30) Foreign Application Priority Data

Sep. 30, 2002 (SE) .................... 0202895

(51) Int. Cl.
*C09K 3/00* (2006.01)
*A61F 2/28* (2006.01)
*A61C 8/00* (2006.01)
*C05B 35/00* (2006.01)

(52) U.S. Cl. ........... 106/35; 106/692; 106/695; 623/23.51; 623/23.56; 433/201.1; 501/127; 501/153

(58) Field of Classification Search ........... 106/692, 106/695, 35; 623/23.51, 23.56; 433/201.1; 501/127, 153
See application file for complete search history.

(56) References Cited

U.S. PATENT DOCUMENTS

| | | | | |
|---|---|---|---|---|
| 4,647,600 A | * | 3/1987 | Kawahara et al. | 523/116 |
| 4,652,593 A | * | 3/1987 | Kawahara et al. | 523/116 |
| 6,620,232 B1 | * | 9/2003 | Kraft et al. | 106/404 |

FOREIGN PATENT DOCUMENTS

| | | |
|---|---|---|
| EP | 0 170 495 A2 | 2/1986 |
| EP | 0 657 398 A1 | 6/1995 |
| SE | 463493 | 10/1990 |
| SE | 010441-1 | 12/2001 |
| WO | PCT/SE99/01803 | 10/1999 |
| WO | WO 01/76534 A1 | 10/2001 |

OTHER PUBLICATIONS

PCT International Search Report, Nov. 11, 2003.

* cited by examiner

*Primary Examiner*—Elizabeth D. Wood
(74) *Attorney, Agent, or Firm*—Young & Thompson

(57) ABSTRACT

An injectable heat generating biocompatible ceramic compositions based on hydraulic calcium aluminate, which can be used for therapeutic treatment in vivo, such as tumour treatment, pain control, vascular treatment, drug activation etc, when curing in situ, and which form a biocompatible solid material that can be left in the body for prolonged periods of time without causing negative health effects, and can also be used to restore the mechanical properties of the skeleton after cancerous diseases as well as in a medical implant, an orthopaedic implant, and a dental implant as a dental filling material.

32 Claims, 1 Drawing Sheet

HEAT GENERATING BIOCOMPATIBLE CERAMIC MATERIALS

THE FIELD OF THE INVENTION

This invention refers to biocompatible ceramic compositions, which before curing show a high degree of formability or mouldability, as well as injectability, and which hardens or cures in-situ under generation of elevated temperatures, the levels of which can be controlled. The compositions according to the present invention, and the elevated temperatures they generate, can e.g. be used for therapeutic purposes in vivo, such as tumour treatment, pain control, vascular treatment, etc.

BACKGROUND OF THE INVENTION

Malignant tumours are traditionally treated by either of three techniques: surgery, radiation or chemotherapy. Often combinations of these techniques are necessary. By surgery, larger tumours of suitable locations may be removed. Surgery alone is however often not enough, due to residues of cancerous tissues and twin tumours. Radiation is used for smaller tumours, particularly in difficult-to-reach locations. By using radiation techniques, surgery may not be necessary. Chemotherapy suffers from other side effects, including necrotic effects on non-cancerous cells.

A therapeutic procedure explored in some fields of surgery is to generate heat in vivo at specific locations in the body, and to benefit from the heat for therapeutic purposes, such as the treatment of cancer cells. Local heat may be achieved by several methods, e.g. with catheters equipped with elements generating heat by electrical resistivity, which can be controlled to desired locations via the vascular system.

An alternative technique to achieve heat in-vivo, is to apply small volumes of slurries or pastes of heat generating materials at the desired locations, e.g. by injection with needles. The material cures injected into the body cures through exothermal chemical reactions and thereby generates the desired temperatures. As the temperature rises, local therapeutic effects are generated. Ideally, when the reactions are completed, the cured substance should form a biocompatible solid material, which can be left for prolonged periods of time in the body without any negative health effects. Only a few types of therapies benefiting from heat generating materials are performed today; the heat generating material being PMMA (polymethylmethacrylate) bone cement, despite the lack of biocompatibility.

Treatment of malignant cancerous tumours, as well as metastasis, myeloms, various cysts, etc, involving the local application of heat generating materials in vivo is used to some degree, although it is still a less frequent treatment technique. The technique involves either local thermal necrosis or restriction of the nutritional or blood feed, or oxygenation, to the tumours or cells.

The use of injectable heat generating materials for cancer treatment is particularly suitable for tumours in the skeleton. The procedure may involve direct injection of a cell-destroying cement; or alternatively the removal of the tumour by surgery, followed by filling of the remaining cavity by an in-situ-curing material. The former procedure offers at least two advantages: One being that increased temperatures during curing reduce the activity of, or kills, residual cancerous tissue. Another effect is that the cement restores the mechanical properties of the skeleton, hence reducing the risk of fractures due to weakened bone.

Injectable pastes are also used in combination with radiation treatment, as when spine vertebrae are first filled with PMMA bone cement injected into the trabecular interior through the pedicles to provide mechanical stability, followed by radiation treatment of the same vertebra.

Similarly, injectable pastes are used for the treatment of collapsed osteoporotic vertebrae. The filling of collapsed vertebrae with bone cement reduces the pain and the dimensions of the vertebrae may be restored. Here the heat generation contributes, in addition to the mechanical stabilization of the vertebrae to the reduction of pain in the spine.

Locally generated heat can be used for the local destruction of nerves to reduce pain, to destroy the function of blood vessels, and to locally trigger the effect of drugs.

As of today, there is no commercialised biocompatible cement, specifically developed for therapeutic purposes by heat generation. Only standard bone cement based on polymethyl methacrylate (PMMA) is used. This material may generate sufficient temperatures, but does not show adequate biocompatibility. Due to lack of better alternatives, PMMA bone cement is however well established in surgery.

Disadvantages With Present Materials

Today's PMMA based bone cements are developed for orthopaedic needs, primarily the fixation of hip and knee implants in the skeleton. Despite many disadvantages, these materials are today established in orthopaedics after several decades of use. There is however an on-going search for better, more biocompatible bone cements.

PMMA based bone cements are not biocompatible materials. They have clear toxic effects caused by leakage of components, such as solvents and non-polymerised monomer. These leakages become particularly high for low viscosity formulations (being injectable) with high amounts of solvents and monomers.

Ideally in cell therapy with heat generating pastes, the volume of cured material left after therapy, shall trigger a minimum of unwanted tissue reactions. This requires a high degree of chemical stability and biocompatibility.

For treatment of cancerous bone, the cured material left in the skeleton ideally possesses mechanical properties similar to those of natural bone. In particular, an insufficient strength or stiffness is disadvantageous for load bearing parts of the skeleton. An orthopaedic cement shall preferably have an elastic modulus of around 10–20 GPa. Today's PMMA bone cements show elastic modulus around 3 GPa.

Today's PMMA bone cements cure while generating heat in amounts considered excessive for normal orthopaedic use. For use in vertebroplasty, some argue that a temperature rise may be advantageous, since it may contribute to reduce pain. However, today's bone cements offer no, or very limited, possibilities for the surgeon to control the generated temperature.

Also cements generating low temperatures rises during curing are of interest. A low temperature bone cement based on hydraulic ceramics is described in the pending Swedish patent application "Ceramic material and process for manufacturing" (SE-0104441-1), filed 27 Dec. 2001. In said patent application the temperature rise due to the hydration reactions is damped by addition of suitable inert, non-hydraulic phases, which are also favourable for the mechanical properties and biocompatibility. However, these ceramic materials do not offer the means to control the heat generation through well controlled phase compositions of the hydrating ceramic, or controlling the temperature by accelerators and retarders.

SUMMARY OF THE INVENTION

In view of the drawbacks associated with the prior art injectable paste compositions, when used for cell therapy, pain control, vascular treatments etc, there is a need for an in-situ curing paste-like material, which can be injected through fine needles into a position in the human body, and which cures during a controlled time span under generation of a controlled amount of heat, triggering various therapeutic effects on targeted tissues and organs, and forming a stable, non-toxic and biocompatible solid volume. For use in the skeleton, the cured material should preferably have mechanical properties similar to those of bone.

To fulfil these needs, the present invention uses hydraulic cements, particularly calcium aluminates, which cure exothermically as a result of chemical reactions with water forming solid ceramic materials of high biocompatibility and suitable mechanical properties.

The objective of the present invention is to provide injectable heat generating ceramic biocement compositions, based on hydraulic oxide ceramics, primarily calcium aluminates, the curing times and temperature increase of which can be controlled to suit clinical needs. After curing, a biocompatible material is formed, which left in the body for prolonged periods of time causes no negative health effects.

A further object of the present invention is to provide compositions which can function as load bearing bone graft material, restoring the mechanical properties of the skeleton after that tumours have been removed or treated by radiation, hence reducing the risk of fractures due to the weakening of the bone.

A further object of the present invention is to use the biocompatible ceramic composition for therapeutic treatment by the heat generated from said compositions.

More particularly, the injectable biocompatible cement compositions according to the present invention can suitably be used for therapeutic purposes in vivo, e.g. for cancer treatment, pain relief, vascular treatment, bone restoration and activation of drugs, by the heat they generate when they cure in situ in the body.

The biocompatible cement compositions according to the present invention can further be used to for manufacturing medical implants, orthopaedic implants, dental implant or used as dental filling material, or The present invention can also be used for manufacturing of drug carrier for drug delivery in a patient's body.

These biocompatible ceramic compositions are in a basic form composed of a hydraulic powder raw material, predominantly comprising calcium aluminate phases; less than 50 vol. %, preferably less than 10 vol. %, of $CA_2$, based on the total volume of the calcium aluminate phases, more than 50 vol. %, preferably more than 90 vol. % of CA and $C_{12}A_7$, based on the total volume of the of calcium aluminate phases, and less than 10 vol. %, preferably less than 3 vol. % of $C_3A$, based on the total volume of the of calcium aluminate phases. The composition according to the present invention may optionally contain suitable additives. The sum of all components amounts to 100%, and the CA-phases amounts to at least 50%, preferably at least 70%, most preferably at least 90%.

The hydraulic powder raw material of the present invention may further comprise the hydraulic powders calcium silicate and/or calcium sulphate in an amount less than 50 vol. % of the total volume of hydraulic ingredients.

The compositions according to the present invention may further comprise a non-hydraulic filler comprising calcium titanate or any other ternary oxide of perovskite structure according to the formula $ABO_3$, where O is oxygen and A and B are metals, or any mixture of such ternary oxides. A in the perovskite structure is selected from the group comprising Mg, Ca, Sr or Ba, and that the B in the perovskite structure is selected from the group comprising Ti, Zr, or Hf. The non-hydraulic filler should be present in an amount of less than 30 vol. %, preferably less than 10 vol. % of the total volume of the ceramic ingredients.

In order to increase the bioactivity of the compositions according to the present invention it may further comprise particles or powder of one or more biocompatible materials selected from the group comprising calcium carbonate, calcium phosphate, apatite, fluoroapatite, carbonates-apatites, and hydroxyapatite, the total amount of which should be less than 30 vol. % of the total volume of the ceramic ingredients.

The grain size of the powder/particle raw material used is predominately less than 20 microns, preferably less than 10 microns, and most preferably less than 3 microns.

The curing of the compositions according to the present invention can be performed in various ways, such as treating the biocompatible ceramic composition with a curing agent, such as a water-based curing liquid or vapour, or by preparing a slurry from said curing liquid and the biocompatible ceramic composition.

The curing agent may comprise additives to enhance the generation of heat by controlling the curing time. These additives can be selected from water reducing agents (an agent that reduces the amount of water necessary to keep a high flowability and to control the viscosity or workability of the ceramic powder slurry, without having to add excessive amounts of water), such as polycarboxylic acids, polyacrylic acids, and superplasticisers, such as Conpac 30®. The additives according to the present invention can further be selected from accelerator agents, which accelerate the hardening process, and are selected from the group comprising lithium chloride, lithium hydroxide, lithium carbonate, lithium sulphate, lithium nitrate, lithium citrate, calcium hydroxide, potassium hydroxide, potassium carbonate, sodium hydroxide, sodium carbonate, sodium sulphate and sulphuric acid. In a preferred embodiment of the present invention the accelerator is LiCl, and in a more preferred embodiment of the present invention LiCl is present in an amount of 10–500 mg in 100 g of curing liquid. Still further additives according to the present invention are retarder agents, which retard the hardening process, and are selected from the group comprising polysaccharide, glycerine, sugars, starch, and cellulose-based thickeners.

When the compositions according to the present invention are used, in particular, as dental material or implants, the compositions may further comprise expansion controlling additives such as fumed silica and/or calcium silicate. The expansion during curing of the material is $\leq 0.8\%$.

When injected or otherwise introduced into a patient's body, the compositions according to the present invention can generate temperatures of 30–150° C. while curing.

When cured, the compositions according to the present invention has a compressive strength of at least 100 MPa.

The present invention further pertains to a cured biocompatible ceramic composition according the above, and also to a medical device comprising said cured biocompatible ceramic composition.

The present invention further pertains to a method for manufacturing the above-described chemically bonded biocompatible ceramic composition, which method comprises preparing a calcium aluminate/powder mixture of selected phase composition and grain size, and curing said mixture by treating the biocompatible ceramic composition with a curing agent, such as a water-based curing liquid or vapour, or by preparing a slurry from said curing liquid and the biocompatible ceramic composition. The method may also comprise the step of removing any residual water or organic contamination from the powder mixture before curing.

The present invention also pertains to a therapeutic method comprising the steps of introducing a biocompatible ceramic composition into a patient's body and curing said composition, whereby heat is generated.

In a preferred embodiment, the method of generating heat in vivo in a patient's body for therapeutical purposes (e.g. cancer treatment, vascular treatment, pain relief, and activation of drugs), comprises the following steps:

preparing a calcium aluminate powder mixture comprising less than 50 vol. %, preferably less than 10 vol. %, of $CA_2$, based on the total volume of the calcium aluminate phases, more than 50 vol. %, preferably more than 90 vol. % of CA and $C_{12}A_7$, based on the total volume of the of calcium aluminate phases, less than 10 vol. %, preferably less than 3 vol. % of $C_3A$, based on the total volume of the of calcium aluminate phases, wherein the CA-phases amounts to at least 50%, preferably at least 70%, most preferably at least 90%, and optionally adding calcium silicate and/or calcium sulphate in an amount less than 50 vol. % of the total volume of hydraulic ingredients, The preferred embodiment of the method according to the present invention optionally comprises adding non-hydraulic filler in an amount of less than 30 vol. %, preferably less than 10 vol. % of the total volume of the ceramic ingredients, optionally adding particles or powder of one or more biocompatible materials, the total amount of which should be less than 30 vol. % of the total volume of the ceramic ingredients, optionally comprises reducing the size of the powder/particle material to less than 20 microns, preferably less than 10 microns, and most preferably less than 3 microns, optionally removing any residual water or organic contamination from the powder mixture, optionally adding viscosity and workability controlling additives such as water reducing agents, expansion controlling additives, curing accelerator and retarder additives.

The preferred embodiment of the method according to the present invention also comprises introducing the above-described composition into the body at a specific location of therapeutic treatment and curing the composition in situ in a patient's body.

The step of curing in the above mentioned method may comprise, prior to the introduction into a patient's body, mixing the biocompatible ceramic composition with a curing agent, thereby obtaining a slurry, and then introduce the slurry into the desired location in said patient. The step of curing can also be performed by introducing the biocompatible ceramic composition into a patient's body and then, in situ at the desired location, treated the composition with a curing agent, such as a water-based solution or water vapour.

BRIEF DESCRIPTION OF THE DRAWINGS

The present invention will become more fully understood from the detailed description given below and the accompanying drawings which are given by way of illustration only, and thus are not limitative of the present invention, and wherein.

DETAILED DESCRIPTION OF THE INVENTION

Figure 1:
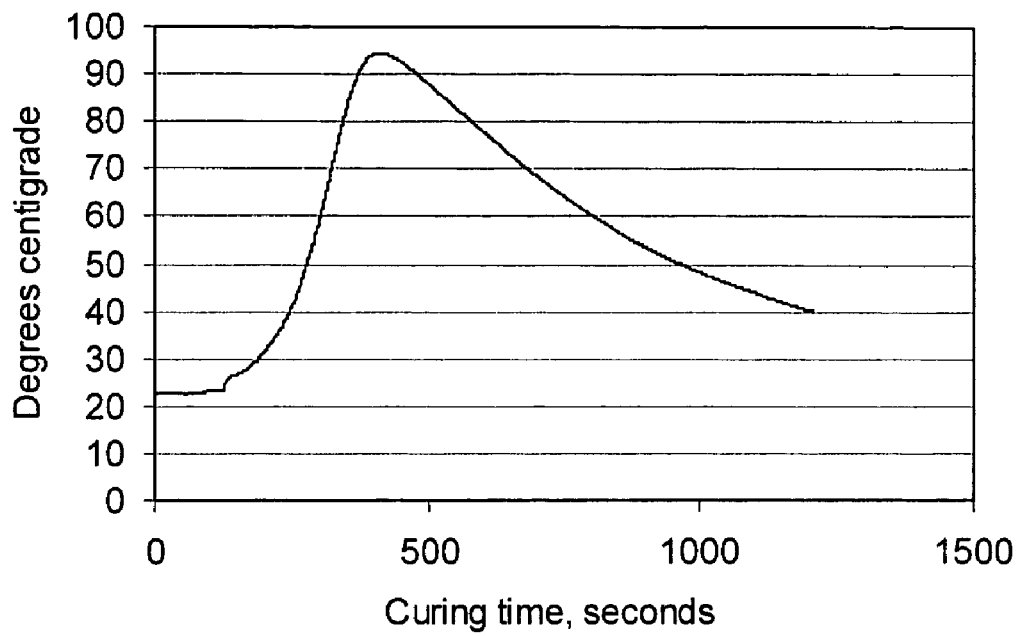
FIG. 1 shows a graph showing the temperature over time generated by a composition according to the present invention having a concentration of 0.4 wt. % of LiCl in the hydrating solution.

The present invention refers to materials, which cure exothermically under generation of controllable amounts of heat, leading to elevated temperatures. The heat-generating materials can be used for therapeutic purposes, involving local heating of cells, cell systems and organs. The material is applied in the form of slurries, pastes or putties to the desired location e.g. by injection, where it cures into a solid body, generating sufficient temperatures to achieve the desired effects, for example for tumour treatment, pain control or vascular treatments. Materials according to the present invention form an alternative to the established PMMA based bone cements.

The material of the invention cures as a result of hydration reactions, between ceramic oxide powders and water. Through the hydration a new, strong binding phase composed of hydrates is formed. Ceramic materials curing through hydration are referred to as hydraulic cements. Hydraulic materials include concretes based on Portland cement as well as special ceramics used in dentistry and orthopaedics. The amount of heat generated during hydration depends on several factors, as is further described below.

The most relevant hydraulic cement of the present invention is calcium aluminate. This material consists of phases from the $CaO-Al_2O_3$ system. Several phases are described in the literature, primarily $C_3A$, $C_{12}A_7$, CA and $CA_2$ (C=CaO, A=$Al_2O_3$), all of which are relevant to the present invention. As an alternative embodiment, calcium silicate may be used according to the invention.

There are several reasons for using calcium aluminates as base substance for injectable bio-cements. In comparison to other water binding systems, e.g. phosphates, carbonates and sulphates of calcium, the aluminates are characterised by high chemical resistance, high strength and controlled curing pace. However, silicates have properties similar to those of aluminates and can also be used according to the present invention. Also, the curing chemistry based on water makes the process relatively unaffected by water-based body fluids. Before hardening, the material has good workability; it can be used both as slurry or paste. Also, the temperature generation of calcium aluminates may be controlled by the details of the phase composition.

Bio-cement compositions based on calcium aluminate which are relevant for the present invention are described in the pending Swedish patent application "Ceramic material and process for manufacturing" (SE-0104441-1), filed 27 Dec. 2001, and in PCT/SE99/01803, "Dimension stable binding agent systems", filed 08 Oct. 1999. All additives disclosed in these patent applications are relevant to the present invention.

If a powder of calcium aluminate is mixed with water or a water-based solution a process starts, which involves the steps of dissolution of the calcium aluminates in the water, forming a solution containing ions of calcium and aluminium. At sufficient ion concentrations, a precipitation of calcium-aluminate hydrates crystallites starts in the liquid. These hydrates build up a new strong binding phase in the cured solid material.

The temperatures reached as the hydraulic cement cures depend on several factors, the most important ones being: the phase composition of the starting calcium aluminate powder, grain size of the starting material powder, the dissolution rate, the hydration rate as controlled by additions of accelerators or retarders, the amount of inert, non-hydraulic phases in the composition, the total volume of hydrating material, and the heat transfer to the environment.

The hydration of calcium aluminates and calcium silicates is a stepwise process. The initially formed hydrates are transformed, in several steps, into more stable hydrate phases. At room temperature the initial hydrate phase is $CaO.Al_2O_3.10H_2O$, abbreviated as $CAH_{10}$ ($C=CaO$, $A=Al_2O_3$, $H=H_2O$). The most stable hydrate phase is $C_3AH_6$. The following reactions have been identified for hydration of CA:

$$CA + 10H \rightarrow CAH_{10} \quad (1)$$

$$2CA + 11H \rightarrow C_2AH_8 + AH_3 \quad (2)$$

$$3CA + 12H \rightarrow C_3AH_6 + 2AH_3 \quad (3)$$

$$2CAH_{10} \rightarrow C_2AH_8 + AH_3 + 9H \quad (4)$$

$$3C_2AH_8 \rightarrow 2C_3AH_6 + AH_3 + 9H \quad (5)$$

All reaction steps are exothermal and heat is developed. The formation of $CAH_{10}$ (step 1) produces 245±5 J/g, $C_2AH_8$ following step 2, 280±5 J/g and $C_3AH_6$ (step 3) 120±5 J/g. The total amount of heat generated by standard calcium aluminate cement, consisting mainly of the phases CA and $CA_2$, is in the range 450 to 500 J/g, as the sum of several hydration steps. The principles of hydration are similar for calcium silicate cements.

The details of the hydration steps are dependent on temperature. The higher the temperature, the more reaction steps may occur within a certain period of time. At room temperature the $CAH_{10}$ hydrate forms fast, but the conversion to $C_3AH_6$ arise very slowly, over a period of months. At body temperature (37° C.), $C_3AH_6$ is formed within a few hours. At 60° C., the stable hydrate forms within minutes. If several reaction steps occur fast during the initial hydration, the generated temperature is higher. A slower hydration generates lower temperatures.

There are also other calcium aluminate phases, primarily $C_3A$, $C_{12}A_7$ and $CA_2$, which hydrate as a result of similar reactions. It has been found that the hydration rate depends on the stoichiometry of the starting phase. The higher the amount of Ca in the starting powder, the faster the hydration proceeds. Thus, $C_3A$ and $C_{12}A_7$ cure faster than CA and $CA_2$. The most probable explanation to this phenomenon is found in the hydration mechanisms, which first involve dissolution of the calcium aluminate into water, followed by precipitation of hydrates as the concentrations of Ca- and Al-ions in the solution reach sufficient levels. For the precipitation of hydrates to be initiated, a higher Ca- than Al-concentration is required.

Any calcium aluminate cement is a mixture of phases. In general, commercially available cements are composed of CA and $CA_2$. The phases $C_3A$, $C_{12}A_7$ are not used in commercial cements. Higher amounts of these fast hydrating calcium aluminate phases however trigger faster hydration and thereby higher temperatures. Additions of these phases can be used to steer the temperature generated in a calcium aluminate based hydraulic ceramic.

The temperatures generated by the calcium aluminate-based hydraulic cements according to the present invention can be controlled approximately to the interval between 30 and 150° C. This entire interval is of relevance for therapeutic applications. Cell necrosis occurs from about 45° C., depending also on exposure time. The volume used for the treatment of osteoporotic spine vertebrae is between 3 and 8 ml. For tumour treatment in the spine typically 1–5 ml is needed. In vascular treatment around 0.5–2 ml is typical.

Controlling the Temperature Rise During Curing

To generate high temperatures during curing of an injectable bio-cement, at least the following factors need to be taken into account:

The choice of phase composition in the hydraulic starting powder, and the hydrates that are formed during the initial curing phase. Calcium aluminate phases rich on Ca hydrate faster. For example, an increased amount of $C_3A$ increases the hydration rate compared to pure CA, and thus higher temperatures. Additions of $CA_2$ to CA reduce the hydration rate. For heat generating materials, compositions with $C_3A$ and $C_{12}A_7$ in addition to CA and $CA_2$ are of particular interest for the present invention.

Of particular interest to the invention are powder compositions with no or very small amounts of $CA_2$ (which cure very slowly). The amount of $CA_2$ should be lower than 50 vol. %, preferably less than 10 vol. %, based on the total of calcium aluminate phases; the majority of the calcium aluminates being CA and $C_{12}A_7$ (with intermediate curing rates), together forming more than 50 vol. %, preferably more than 90 vol. %. In addition a smaller part of $C_3A$ is desired, acting as accelerator or trigger for the curing. The amount of $C_3A$ should be less than 10 vol. %, preferably less than 3 vol. % of the total amount of calcium aluminate phases. It is unique for the present invention to control the temperature generation of relevant volumes of material by choosing phase compositions within said intervals.

The grain size of the starting powder. Smaller grains dissolve and hydrate faster, and thereby generate higher temperatures. The grain size is controlled by pre-treatment of the hydraulic cement powder with size reducing methods, e.g. milling. The powder grain size is preferably less than 10 microns, more preferably less than 3 microns.

The hydration rate is controlled by the addition of accelerator agents and/or retarder agents. There are several accelerating additives known in the field, e.g. Li-salts such as lithium chloride; as well as retarders, e.g. sugar and various hydrocarbons. With combinations of accelerators and retarders special curing effects may be achieved, characterised by a period of no or very slow curing, followed by a delayed stage of fast hydration; a curing cycle of exponential character.

In the present invention, accelerators and retarders are not primarily used to control curing time, as known within the field, but rather to control the temperature generation.

Of particular interest are compositions cured with LiCl solutions with about 10–500 mg of LiCl in 100 g of water; as well as compositions cured with solutions containing combinations of accelerators and retarders, e.g. LiCl and sugar, respectively.

Examples of other salts that may be used as accelerators according to the present invention are: lithium hydroxide, lithium carbonate, lithium sulphate, lithium nitrate, lithium citrate, calcium hydroxide, potassium hydroxide, potassium carbonate, sodium hydroxide, sodium carbonate, sodium sulphate and sulphuric acid.

Examples of retarders that can be used according to the present invention are glycerine, polysaccharide, sugars, starch, and cellulose-based thickeners.

The ceramic compositions according to the present invention further comprises a component which is a water reducing agent based on a compound selected from the group comprising polycarboxylic acids, polyacrylic acids, and superplasticisers, such as Conpac 30®.

The amount of inert, non-hydraulic phases in the cement composition. Non-hydraulic phases, e.g. non-hydrating oxides, other ceramics or metals, may be added for purposes such as increased mechanical strength and dimensional stability during hydration. However, for increased temperature generation the amount of non-hydraulic phases should be kept low. Non-hydraulic phase concentrations of less than 30 vol. % are of relevance to the invention, preferably the amount should be less than 10 vol. % of the total of ceramic ingredients. In addition, non-hydraulic additives may also affect the hydration rate.

Also, the total volume of hydrating material and the heat transfer to the environment have an influence on the temperature that can be obtained. The volume specific heat generation therefore needs to be higher for smaller volumes of bio-cement, to reach the same temperature. Or inversely, larger volumes of cement are beneficial to generate high temperatures.

EXAMPLES

Example 1

This example describes the manufacturing procedure of a ceramic cement consisting of hydrated calcium aluminate without fillers, and serves to illustrate the effect of hydration rate on the generated temperatures. Note that the achieved temperatures also depend on other factors, such as volume of cured material and heat transportation to the environment.

As raw material, the commercial product Ternal White® from Lafarge Aluminates, is used. This is a calcium aluminate with an $Al_2O_3/CaO$-ratio of about 70/30.

The first preparation step was to reduce the grain size of the powder. This was achieved by ball milling. The milling was performed with a rotating cylindrical plastic container filled to ⅓ of its volume with Ternal White powder, and ⅓ with inert silicon nitride milling spheres having a diameter of 10 mm. The milling liquid was iso-propanol, and the total milling time 72 hrs. This milling reduced the size of 90% of the grains to less than 10 µm.

After milling, the milling spheres were removed by sieving and the alcohol evaporated. Thereafter the milled powder was burnt at 400° C. for 4 hours, to remove any residual water and organic contamination.

The second step was to prepare a hydration solution. The solution consisted of de-ionised water, to which a water reducing agent and an accelerator was added. The water reducing agent was selected from a group of commercial so called superplasticisers, Conpac 30® from Perstorp AB, known within the field, but any other similar agent would also function. The superplasticiser was added to a concentration of 1 wt. % in the water. The accelerator LiCl was added in concentrations of 0.05, 0.08, 0.2 or 0.4 wt. %

The prepared Ternal White powder and the water solutions were mixed so that the ratio of the weight of water to the weight of milled Ternal White® powder was 0.35. The powder-liquid mixtures were cured in 10 ml plastic containers in air, and the temperature development was recorded with a thermocouple introduced into the centre of the cement volume.

Figure 2:
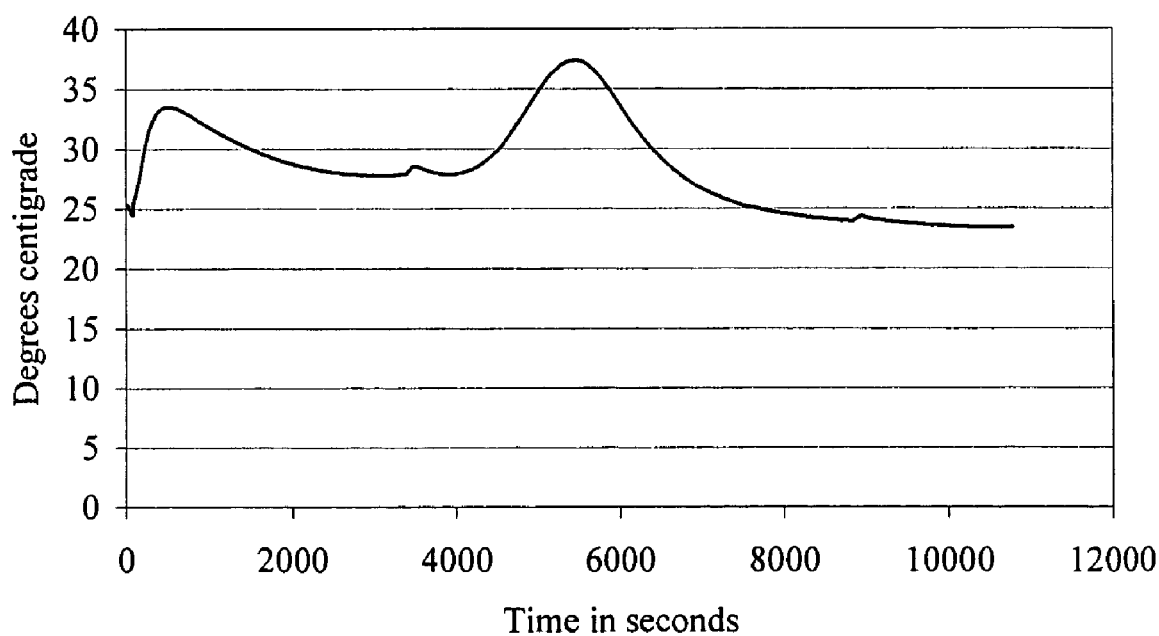
FIG. 2 shows a graph showing the temperature over time generated by a composition according to the present invention having a concentration of 0.05 wt. % of LiCl in the hydrating solution.

The results are provided in FIGS. 1 and 2. FIG. 1 shows that a concentration of 0.4 wt. % of LiCl in the hydrating solution produces above 90° C. during curing in a room temperature environment, while FIG. 2 illustrates the much lower temperatures achieved with a LiCl concentration of 0.05 wt. %, as well as the slower hydration rate.

This example only serves to illustrate the curing rate effect as achieved by additions of curing accelerators, in this case LiCl, on the temperature.

Example 2

This example describes the different curing rates typical for calcium aluminates of different phases of calcium aluminate.

Three different calcium aluminate powders composed to 99% of the pure phases CA, $C_{12}A_7$, $CA_3$ are used as starting materials.

Powder grain sizes of less than 10 µm were achieved by milling, as described in Example 1. The milled powders were also burnt at 400° C. for 4 hours, to remove any residuals.

De-ionised water without any additives was used as hydration liquid.

The prepared powders were mixed with water keeping the ratio of water to powder constant at 0.35, by weight. The powder-water mixtures were cured in 10 ml plastic containers in air at room temperature.

The hydration rates for the CA, $C_{12}A_7$, $CA_3$ phases, measured as time to solidification, were measured to 4–6 hours, 5–10 minutes and 2–4 seconds, respectively.

The invention claimed is:

1. A biocompatible ceramic composition comprised of powdered calcium aluminate phases of the following composition:
   less than 50 vol. %, but greater than zero, of $CA_2$, based on the total volume of the calcium aluminate phases;
   more than 50 vol. % of a mixture of CA and $C_{12}A_7$ together based on the total volume of the calcium aluminate phases;
   less than 10 vol. %, but greater than zero, of $C_3A$, based on the total volume of the calcium aluminate phases; and
   optionally additives, wherein,
   the sum of all components amounts to 100%, and wherein the CA-phases amounts to at least 50%, and
   the biocompatible ceramic composition generates temperatures of 30–150° C. when cured in a living human body.

2. The biocompatible ceramic composition according to claim 1, further comprising the hydraulic powders calcium silicate and/or calcium sulphate in an amount less than 50 vol. % of the total volume of hydraulic ingredients.

3. The biocompatible ceramic composition according to claim 1, further comprising particles or powder of one or more biocompatible materials selected from the group consisting of calcium carbonate, calcium phosphate, apatite, fluoroapatite, carbonates-apatites, and hydroxyapatite in a total amount less than 30 vol. % of the total volume of the ceramic ingredients.

4. The biocompatible ceramic composition according to claim 1, further comprising a component which is a water reducing agent selected from the group consisting of polycarboxylic acids, polyacrylic acids, and superplasticisers.

5. The biocompatible ceramic composition according to claim 1, further comprising expansion controlling additives.

6. The biocompatible ceramic composition according to claim 1, further comprising a water-based curing liquid.

7. The biocompatible ceramic composition according to claim 6, wherein the curing liquid further comprises an accelerator agent which accelerates the hardening process, which accelerator agent is selected from the group consisting of lithium chloride, lithium hydroxide, lithium carbonate, lithium sulphate, lithium nitrate, lithium citrate, calcium hydroxide, potassium hydroxide, potassium carbonate, sodium hydroxide, sodium carbonate, sodium sulphate and sulphuric acid.

8. The biocompatible ceramic material according to claim 7, wherein LiCl is present in an amount of 10–500 mg in 100 g of curing liquid.

9. The biocompatible ceramic composition according to claim 6, wherein the curing liquid further comprises a retarder agent which retards the hardening process, which retarder agent is selected from the group consisting of polysaccharide, glycerine, sugars, starch, and cellulose-based thickeners.

10. The biocompatible ceramic composition according to claim 1, wherein the grain size of the powdered material used is predominately less than 20 microns.

11. The biocompatible ceramic composition according to claim 1, having a compressive strength of at least 100 MPa.

12. The biocompatible ceramic composition according to claim 1, the composition being cured.

13. A method for manufacturing a biocompatible ceramic composition according to claim 1, comprising the steps of:
preparing a calcium aluminate/powder mixture of selected phase composition and grain size; and
curing said mixture by treating the biocompatible ceramic composition with a curing agent, or by preparing a slurry from said water-based curing liquid and the biocompatible ceramic composition, wherein,
the amount of $CA_2$ and the amount of $C_3A$ is selected for achieving temperatures up to 150° C. during use and so that the biocompatible ceramic composition generates a controlled amount of heat at temperatures of 30–150° C. when cured in a living human body.

14. A medical implant comprising the biocompatible ceramic composition according to claim 1.

15. An orthopaedic implant comprising the biocompatible ceramic composition according to claim 1.

16. A medical implant comprising the biocompatible ceramic composition according to claim 2.

17. An orthopaedic implant comprising the biocompatible ceramic composition according to claim 2.

18. A medical implant comprising the biocompatible ceramic composition according to claim 3.

19. An orthpaedic implant comprising the biocompatible ceramic composition according to claim 3.

20. A medical implant comprising the biocompatible ceramic composition according to claim 4.

21. An orthopaedic implant comprising the biocompatible ceramic composition according to claim 4.

22. A medical implant comprising the biocompatible ceramic composition according to claim 5.

23. An orthopaedic implant comprising the biocompatible ceramic composition according to claim 5.

24. A medical implant comprising the biocompatible ceramic composition according to claim 6.

25. An orthopaedic implant comprising the biocompatible ceramic composition according to claim 6.

26. A medical implant comprising the biocompatible ceramic composition according to claim 7.

27. An orthopaedic implant comprising the biocompatible ceramic composition according to claim 7.

28. A medical implant comprising the biocompatible ceramic composition according to claim 8.

29. An orthopaedic implant comprising the biocompatible ceramic composition according to claim 8.

30. A medical implant comprising the biocompatible ceramic composition according to claim 9.

31. The biocompatible ceramic composition of claim 1, with at least an effective amount for achieving high temperatures during use and less than 3 vol. % of $C_3A$, based on the total volume of the of calcium aluminate phases.

32. A biocompatible ceramic composition comprised of powdered calcium aluminate phases of the following composition:
less than 50 vol. %, but greater than zero, of $CA_2$, based on the total volume of the calcium aluminate phases;
more than 50 vol. %, but groator than zora, of a mixture of CA and $C_{12}A_7$ together based on the total volume of the calcium aluminate phases;
at least an effective, non-zero, amount of $C_3A$ for achieving temperatures up to 150° C. during use and less than 10 vol. %, but greater than zero, of $C_3A$, based on the total volume of the calcium aluminate phases; and
optionally additives, wherein,
the sum of all components amounts to 100%, and wherein the CA-phases amounts to at least 50%, and
the biocompatible ceramic composition generates temperatures of 30–150° C. when cured in a living human body.

* * * * *